(12) United States Patent
Voss et al.

(10) Patent No.: US 8,603,137 B2
(45) Date of Patent: Dec. 10, 2013

(54) METHODS AND SYSTEMS FOR ESTABLISHING HEMOSTASIS RELATIVE TO A PUNCTURE

(75) Inventors: Laveille Kao Voss, Belmont, CA (US); Aaron M. Fortson, Cupertino, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/917,195

(22) Filed: Nov. 1, 2010

(65) Prior Publication Data
US 2012/0109189 A1 May 3, 2012

(51) Int. Cl.
*A61B 17/08* (2006.01)
*A61D 1/00* (2006.01)

(52) U.S. Cl.
USPC .......................................................... 606/213

(58) Field of Classification Search
USPC .................. 606/213, 215, 216, 219, 220, 151
See application file for complete search history.

(56) References Cited

U.S. PATENT DOCUMENTS

| | | | |
|---|---|---|---|
| 2,449,235 A | 9/1948 | Krupp | |
| 3,766,610 A | 10/1973 | Thorsbakken | |
| 4,156,574 A | 5/1979 | Boden | |
| 4,807,333 A | 2/1989 | Boden | |
| 5,292,332 A * | 3/1994 | Lee | 606/213 |
| 5,342,393 A * | 8/1994 | Stack | 606/213 |
| 5,417,699 A | 5/1995 | Klein et al. | |
| 5,435,044 A | 7/1995 | Ida | |
| 5,454,140 A | 10/1995 | Murai | |
| 5,478,353 A * | 12/1995 | Yoon | 606/213 |
| 5,520,070 A | 5/1996 | Beugelsdyk et al. | |
| 5,520,702 A | 5/1996 | Sauer et al. | |
| 5,562,689 A | 10/1996 | Green et al. | |
| 5,569,306 A | 10/1996 | Thai | |
| 5,572,770 A | 11/1996 | Boden | |
| 5,630,824 A | 5/1997 | Hart | |
| 5,658,313 A | 8/1997 | Thal | |
| 5,702,397 A | 12/1997 | Goble et al. | |
| 5,725,529 A | 3/1998 | Nicholson et al. | |
| 5,779,707 A * | 7/1998 | Bertholet et al. | 606/75 |
| 5,893,856 A * | 4/1999 | Jacob et al. | 606/151 |
| 5,902,311 A | 5/1999 | Andreas et al. | |
| 5,941,901 A | 8/1999 | Egan | |
| 6,086,608 A | 7/2000 | Ek et al. | |
| 6,099,547 A | 8/2000 | Gellman et al. | |

(Continued)

FOREIGN PATENT DOCUMENTS

| | | |
|---|---|---|
| WO | WO 02/015795 | 2/2002 |
| WO | WO 2005/027754 | 3/2005 |

OTHER PUBLICATIONS

U.S. Appl. No. 13/022,246, filed Feb. 7, 2011, Yribarren.
U.S. Appl. No. 13/035,939, filed Feb. 26, 2011, Ehrenreich.

(Continued)

*Primary Examiner* — Dianne Dornbusch
(74) *Attorney, Agent, or Firm* — Workman Nydegger; Randy Shen

(57) ABSTRACT

Systems and methods for establishing hemostasis relative to a puncture in a lumen wall. A closure device includes a proximal portion and a distal portion. The proximal portion or distal portion rotates during deployment to either close a puncture or plug a puncture to establish hemostasis. A method includes positioning a closure device in a deployment device, positioning the closure device in the tissue tract, and actuating the deployment device to establish relative rotation between the distal portion and the proximal portion of the closure device.

16 Claims, 15 Drawing Sheets

(56) References Cited

U.S. PATENT DOCUMENTS

| | | | |
|---|---|---|---|
| 6,136,010 A | 10/2000 | Modesitt et al. | |
| 6,200,329 B1 | 3/2001 | Fung et al. | |
| 6,206,895 B1 | 3/2001 | Levinson | |
| 6,231,592 B1 | 5/2001 | Bonutti et al. | |
| 6,245,080 B1 | 6/2001 | Levinson | |
| 6,277,140 B2 * | 8/2001 | Ginn et al. | 606/213 |
| 6,398,796 B2 | 6/2002 | Levinson | |
| 7,011,400 B2 | 3/2006 | Nakano | |
| 7,662,161 B2 * | 2/2010 | Briganti et al. | 606/151 |
| 7,713,284 B2 * | 5/2010 | Crofford | 606/219 |
| 7,947,062 B2 * | 5/2011 | Chin et al. | 606/213 |
| 8,100,923 B2 | 1/2012 | Paraschac et al. | |
| 8,128,653 B2 * | 3/2012 | McGuckin et al. | 606/213 |
| 2001/0044638 A1 | 11/2001 | Levinson et al. | |
| 2001/0044639 A1 | 11/2001 | Levinson | |
| 2002/0002401 A1 | 1/2002 | McGuckin, Jr. et al. | |
| 2002/0077658 A1 * | 6/2002 | Ginn | 606/213 |
| 2002/0082641 A1 * | 6/2002 | Ginn et al. | 606/213 |
| 2002/0107542 A1 | 8/2002 | Kanner et al. | |
| 2002/0151921 A1 * | 10/2002 | Kanner et al. | 606/190 |
| 2002/0169478 A1 | 11/2002 | Schwartz et al. | |
| 2002/0188318 A1 * | 12/2002 | Carley et al. | 606/213 |
| 2003/0093096 A1 * | 5/2003 | McGuckin et al. | 606/157 |
| 2003/0144695 A1 * | 7/2003 | McGuckin et al. | 606/213 |
| 2003/0167062 A1 | 9/2003 | Gamabale et al. | |
| 2003/0199987 A1 | 10/2003 | Berg et al. | |
| 2004/0158309 A1 | 8/2004 | Wachter et al. | |
| 2005/0038500 A1 | 2/2005 | Boylan et al. | |
| 2005/0205640 A1 | 9/2005 | Milliman | |
| 2006/0190037 A1 * | 8/2006 | Ginn et al. | 606/213 |
| 2006/0235505 A1 | 10/2006 | Oepen et al. | |
| 2006/0241579 A1 * | 10/2006 | Kawaura et al. | 606/39 |
| 2006/0265008 A1 * | 11/2006 | Maruyama et al. | 606/232 |
| 2006/0265010 A1 | 11/2006 | Paraschac et al. | |
| 2007/0010853 A1 * | 1/2007 | Ginn et al. | 606/213 |
| 2007/0255317 A1 | 11/2007 | Fanton et al. | |
| 2007/0270904 A1 * | 11/2007 | Ginn | 606/213 |
| 2007/0276433 A1 * | 11/2007 | Huss | 606/213 |
| 2007/0276488 A1 | 11/2007 | Wachter et al. | |
| 2008/0312740 A1 | 12/2008 | Wachter et al. | |
| 2009/0157102 A1 * | 6/2009 | Reynolds et al. | 606/142 |
| 2009/0306671 A1 | 12/2009 | McCormack et al. | |
| 2010/0256670 A1 * | 10/2010 | Ginn et al. | 606/213 |
| 2011/0029012 A1 | 2/2011 | Tegels | |
| 2012/0184991 A1 | 7/2012 | Paraschac et al. | |

OTHER PUBLICATIONS

U.S. Appl. No. 13/219,004, filed Aug. 26, 2011, Roorda.
U.S. Appl. No. 13/022,246, May 11, 2012, Office Action.
U.S. Appl. No. 60/502,925, Sep. 15, 2003, Paraschac.
U.S. Appl. No. 13/219,004, Feb. 14, 2013, Office Action.
U.S. Appl. No. 13/219,004, filed Aug. 9, 2013, Office Action.

* cited by examiner

METHODS AND SYSTEMS FOR ESTABLISHING HEMOSTASIS RELATIVE TO A PUNCTURE

FIELD OF THE INVENTION

The present invention relates generally to medical devices. More particularly, embodiments of the invention relate to devices, apparatuses, and methods for establishing hemostasis at an arteriotomy site.

BACKGROUND OF THE INVENTION

Catheterization and interventional procedures, such as angioplasty or stenting, are generally performed by inserting a hollow needle through a patient's skin and tissue into the vascular system. A guide wire may be advanced through the needle and into the patient's blood vessel accessed by the needle. The needle is then removed, enabling an introducer sheath to be advanced over the guide wire into the vessel, e.g., in conjunction with or subsequent to a dilator.

A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath are removed, leaving a puncture site in the vessel wall. Traditionally, external pressure is applied to the puncture site until clotting and wound sealing occur. However, the patient must often remain bedridden for a substantial period of time after clotting to ensure closure of the wound. This procedure, however, may be time consuming and expensive, requiring as much as an hour of a care provider's time. It is also uncomfortable for the patient and requires that the patient remain in the operating room, catheter lab, or holding area. In addition, a risk of hematoma exists from bleeding before hemostasis occurs.

BRIEF SUMMARY

Embodiments of the invention relate to systems and methods for establishing hemostasis relative to a puncture in a body lumen wall. Establishing hemostasis relative to a puncture in a body lumen wall often begins by positioning a closure device, which has a proximal portion and a distal portion, in a distal end of a deployment device. After positioning the closure device in the deployment device, the closure device is positioned in a tissue tract in proximity with the puncture in the body lumen wall with the deployment device. The deployment device is then actuated to establish relative rotation between the distal portion and the proximal portion of the closure device to establish hemostasis relative to the puncture. In some embodiments, the closure device can establish hemostasis by closing the puncture or by plugging the puncture.

In one example, a distal portion of the closure device has tissue engagement features associated therewith. A biasing member coupling the distal portion and the proximal portion of the closure device, is configured to resiliently move between a pre-deployed state and a deployed state. Movement of the biasing member between the deployed state and the pre-deployed state causes relative rotation between the distal portion and the proximal portion to establish hemostasis relative to the puncture in the lumen wall.

In another example, a distal portion has a distal access port defined therein and a proximal portion has a proximal access port defined therein. During deployment, the distal access port and the proximal access port are positioned such that relative rotation between the distal portion and the proximal portion moves the distal access port and the proximal access port into alignment to provide a lumen through the closure device and out of alignment to prevent a flow of fluid through the distal portion.

In some embodiments, a system for establishing hemostasis includes a deployment device that cooperates with the closure device. The deployment device may include a locking feature. When the locking feature is released, a biasing member coupling the distal portion and the proximal portion is released to establish hemostasis. In another example, the deployment device may include a rotational element that engages with and rotates the proximal portion relative to the distal portion to establish hemostasis relative to the puncture.

The accompanying figures, which are incorporated in and constitute part of this specification, are included to illustrate and provide a further understanding of the method and system of the invention. Together with the description, the figures serve to explain the principles of the invention.

BRIEF DESCRIPTION OF THE DRAWINGS

In order to describe the manner in which the above-recited and other advantages and features of the invention can be obtained, a more particular description of the invention briefly described above will be rendered by reference to specific examples thereof that are illustrated in the appended drawings. Understanding that these drawings depict only typical examples of the invention and are not therefore to be considered to be limiting of its scope, the invention will be described and explained with additional specificity and detail through the use of the accompanying drawings.

Figure 1:
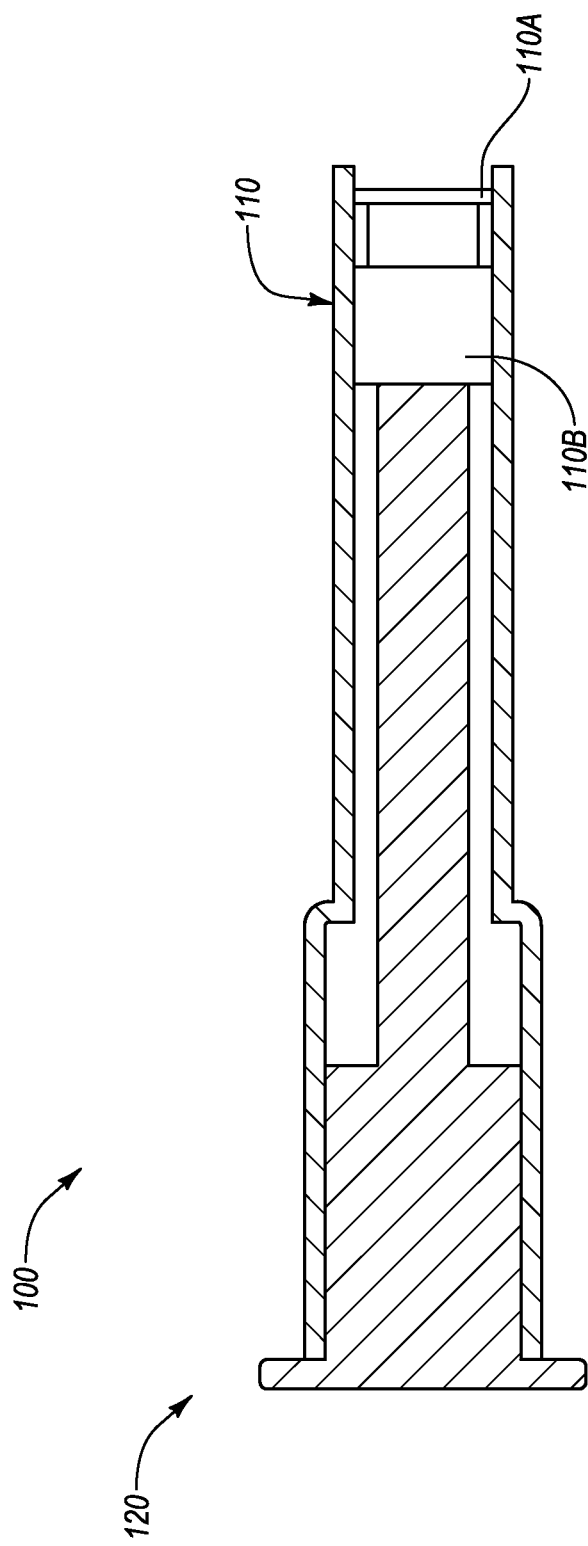
FIG. 1 is a schematic view of a system for closing a puncture in a body lumen wall according to one example.

It should be noted that the figures are not drawn to scale and that elements of similar structures or functions are generally represented by like-reference numerals for illustrative purposes throughout the figures. It also should be noted that the figures are only intended to facilitate the description of examples of the present invention.

DETAILED DESCRIPTION

Devices and methods are disclosed herein for managing access through tissue. In particular, several examples are described below in which a device may be deployed to establish hemostasis in an opening in a body lumen by rotating one portion of the device relative to another portion of the device. Embodiments of the invention further relate to closure devices that can be rotated to establish a state of hemostasis. In some embodiment, the closure device includes a proximal portion and a distal portion. This distal portion is configured to interact with or proximate to the lumen wall. Once the closure device is properly positioned, the distal portion and proximal portion can be rotated relative to each other. In some instances, it is the distal portion that rotates while in other instance, it is the proximal portion that rotates.

The distal portion may be configured to engage with the lumen wall in a manner that closes the puncture by bringing the sides of the puncture together. This can be achieved, for example, when the distal portion engages the lumen wall around the puncture and then rotates to effectively seal the puncture by bringing sides of the lumen wall or the puncture together—thereby closing the puncture to establish hemostasis.

In some embodiments, the distal portion may act as a plug, thereby filling the puncture to establish hemostasis. In these embodiments, the plug may include a port that is used during deployment, but which permits passage of fluid. Hemostasis is then established by rotating the proximal portion (or the distal portion) to close the port and establish hemostasis.

Biodegradable, as defined herein, means the composition will degrade or erode in vivo to form smaller chemical species. Degradation can result, for example, by enzymatic, chemical, and physical processes. Suitable biocompatible, biodegradable polymers include, by way of example only, poly(lactide)s, poly(glycolide)s, poly(lactide-co-glycolide)s, poly(lactic acid)s, poly(glycolic acid)s, poly(lactic acid-co-glycolic acid)s, polyanhydrides, polyorthoesters, polyetheresters, polycaprolactone, polyesteramides, magnesium, magnesium allows, blends and copolymers thereof.

The closure devices described herein may be manufactured from any suitable material. For example, a closure device may be, at least partially, formed from various materials including, but not limited to, bio-degradable materials or bio-absorbable materials, nickel titanium and/or alloys thereof, stainless steel, cobalt chromium and/or alloys thereof, niobium tantalum and/or alloys thereof, other materials suitable for closure devices and/or combinations thereof. Further, a closure device may be, at least partially, formed of or include a radiopaque material and/or be coated with a radiopaque material to enhance visibility of the body lumen filter and/or the anchors.

These materials may include at least one beneficial agent incorporated into the material and/or coated over at least a portion of the material. The beneficial agents may be applied to body lumen filters that have been coated with a polymeric compound. Incorporation of the compound or drug into the polymeric coating of the closure device can be carried out by dipping the polymer-coated body lumen filter into a solution containing the compound or drug for a sufficient period of time (such as, for example, five minutes) and then drying the coated body lumen filter, preferably by means of air drying for a sufficient period of time (such as, for example, 30 minutes). The polymer-coated body lumen filter containing the beneficial agent may then be delivered to a body vessel or other location.

The pharmacologic agents that can be effective in preventing restenosis can be classified into the categories of anti-proliferative agents, anti-platelet agents, anti-inflammatory agents, anti-thrombotic agents, and thrombolytic agents. Anti-proliferative agents may include, for example, crystalline rapamycin. These classes can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, such as, for example, daunorubicin, daunomycin, and plicamycin. Other sub-classes of anti-mitotic agents include anti-mitotic alkylating agents, such as, for example, tauromustine, bofumustine, and fotemustine, and anti-mitotic metabolites, such as, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, such as, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIIbIIIa or $\alpha v\beta 3$, antibodies that block binding to gpIIaIIIb or $\alpha v\beta 3$, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

Anti-inflammatory agents can also be used. Examples of these include, but are not limited to, prednisone, dexamethasone, hydrocortisone, estradiol, fluticasone, clobetasol, and non-steroidal anti-inflammatories, such as, for example, acetaminophen, ibuprofen, naproxen, and sulindac. Other examples of these agents include those that inhibit binding of cytokines or chemokines to the cognate receptors to inhibit pro-inflammatory signals transduced by the cytokines or the chemokines Representative examples of these agents include, but are not limited to, anti-IL1, anti-IL2, anti-IL3, anti-IL4, anti-IL8, anti-IL15, anti-IL18, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, such as, for example, heparin, heparin sulfate, low molecular weight heparins, such as, for example, the compound having the trademark Clivarin®, and synthetic oligosaccharides, such as, for example, the compound having the trademark Arixtra®. Also included are direct thrombin inhibitors, such as, for example, melagatran, ximelagatran, argatroban, inogatran, and peptidomimetics of binding site of the Phe-Pro-Arg fibrinogen substrate for thrombin. Another class of anti-thrombotic agents that can be delivered is factor VII/VIIa inhibitors, such as, for example, anti-factor VII/VIIa antibodies, rNAPc2, and tissue factor pathway inhibitor (TFPI).

Thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

One or more immunosuppressant agents may be used. Immunosuppressant agents may include, but are not limited to, IMURAN® azathioprine sodium, brequinar sodium, SPANIDIN® gusperimus trihydrochloride (also known as deoxyspergualin), mizoribine (also known as bredinin), CELLCEPT® mycophenolate mofetil, NEORAL® Cylosporin A (also marketed as different formulation of Cyclosporin A under the trademark SANDIMMUNE®), PROGRAF® tacrolimus (also known as FK-506), sirolimus and RAPAMUNE®, leflunomide (also known as HWA-486), glucocorticoids, such as prednisolone and its derivatives, antibody therapies such as orthoclone (OKT3) and Zenapax®, and antithymyocyte globulins, such as thymoglobulins. In addition, a crystalline rapamycin analog, A-94507, SDZ RAD (a.k.a. Everolimus), and/or other immunosuppressants.

The materials above can be used to form closure devices or in the formation of closure devices using any number of processes, such as molding, etching, depositing, laser cutting, shape-set memory procedures, fastening operations, any number and combinations of processes.

In one embodiment, the medical devices disclosed herein can include a material made from any of a variety of known suitable materials, such as a shaped memory material ("SMM") or superelastic material. For example, the SMM can be shaped in a manner that allows for restriction to induce a substantially tubular, linear orientation while within a delivery shaft (e.g., delivery catheter or encircling an expandable member), but can automatically retain the memory shape of the medical device once extended from the delivery shaft. SMMs have a shape memory effect in which they can be made to remember a particular shape. Once a shape has been remembered, the SMM may be bent out of shape or deformed and then returned to its original shape by unloading from strain or heating. SMMs can be shape memory alloys ("SMA") or superelastic metals comprised of metal alloys, or shape memory plastics ("SMP") comprised of polymers.

An SMA can have any non-characteristic initial shape that can then be configured into a memory shape by heating the SMA and conforming the SMA into the desired memory shape. After the SMA is cooled, the desired memory shape can be retained. This allows for the SMA to be bent, straightened, compacted, and placed into various contortions by the application of requisite forces; however, after the forces are released, the SMA can be capable of returning to the memory shape. The main types of SMAs are as follows: copper-zinc-aluminium; copper-aluminium-nickel; nickel-titanium ("NiTi") alloys known as nitinol; and cobalt-chromium-nickel alloys or cobalt-chromium-nickel-molybdenum alloys known as elgiloy. The nitinol and elgiloy alloys can be more expensive, but have superior mechanical characteristics in comparison with the copper-based SMAs. The temperatures at which the SMA changes its crystallographic structure are characteristic of the alloy, and can be tuned by varying the elemental ratios.

For example, the primary material of the of a device can be of a NiTi alloy that forms superelastic nitinol. Nitinol materials can be trained to remember a certain shape, straightened in a shaft, catheter, or other tube, and then released from the catheter or tube to return to its trained shape. Also, additional materials can be added to the nitinol depending on the desired characteristic.

An SMP is a shape-shifting plastic that can be fashioned into the devices disclosed herein in accordance with the present invention. When an SMP encounters a temperature above the lowest melting point of the individual polymers, the blend makes a transition to a rubbery state. The elastic modulus can change more than two orders of magnitude across the transition temperature ("$T_{tr}$"). As such, an SMP can be formed into a desired shape of a medical device by heating it above the $T_{tr}$, fixing the SMP into the new shape, and cooling the material below $T_{tr}$. The SMP can then be arranged into a temporary shape by force and then resume the memory shape once the force has been applied. Examples of SMPs include, but are not limited to, biodegradable polymers, such as oligo (ε-caprolactone)diol, oligo(ρ-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present invention.

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

FIG. 1 illustrates a system 100 for closing a puncture in a body lumen wall that includes a twisting closure device 110 and a deployment device 120. The closure device 110 includes a distal portion 110A and a proximal portion 110B. The deployment device 120 is configured to position the closure device 110 within a tissue tract and in proximity with a puncture in a body lumen wall.

The deployment device 120 is further configured to cause relative rotation between the distal portion 110A and the proximal portion 110B to establish hemostasis through the tissue tract. Accordingly, the deployment device 120 can cause the proximal portion 110B to rotate relative to the distal portion 110A, the proximal portion 110B to rotate relative to the distal portion 110A or the proximal portion 110B and the distal portion 110A to both rotate.

Several exemplary closure devices and deployment devices will be described in more detail below as well as exemplary methods for closing punctures in the body lumen wall using the closure devices. The relative sizes of the elements of the closure devices, deployment devices, and body lumens is provided for ease of reference only and are not necessarily to scale. Further, the relative motion, including rotation of the elements relative to other elements are also provided for ease of reference only and are not necessarily to scale.

In some embodiments, the rotation of a portion of the closure devices disclosed herein is achieved by creating a force that, when released, causes rotation needed to seal or close a puncture. As a result, spring arms or other structures which act as loaded springs can be employed to achieve such rotation. In this case, the state of the closure device is maintained by the same spring force. By way of example, the rotation can be achieved by forming the spring arms or other structure using a shaped memory material or a superelastic material.

In some embodiments, the rotation may be achieved with a rotational element that interacts with the closure device to rotate a portion of the closure device. The state of the closure device after deployment can be maintained by structure of the closure element itself. For example, a proximal portion may engage with a distal portion in a manner that prevents rotation unless a sufficient torque is applied. In this case, sufficient torque can be applied to initially rotate a portion of the closure device, thus establishing hemostasis. Restenosis is prevented because sufficient force to rotate a portion of the closure device is no longer present after deployment. The following discussion illustrates examples of closure devices for establishing hemostasis from a puncture.

Figure 2A:
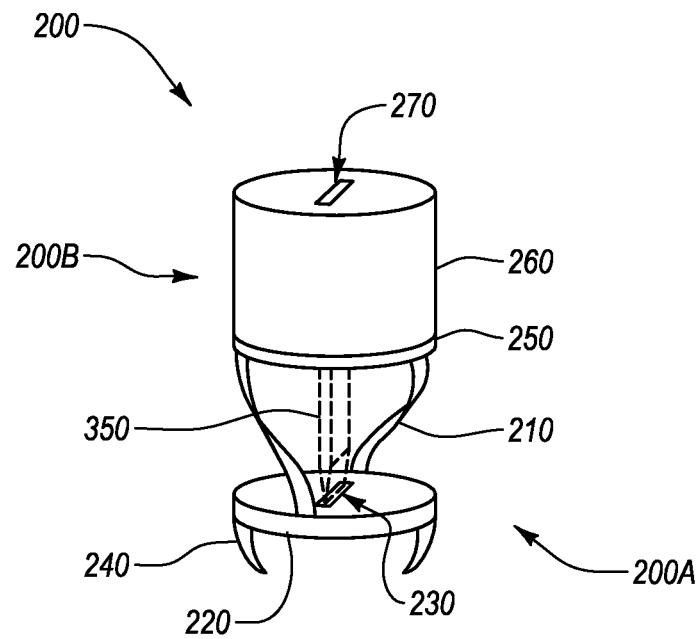
FIG. 2A illustrates a device for closing a puncture in a body lumen wall in a first state according to one example.

FIG. 2A illustrates a closure device 200 configured to close a puncture in a body lumen wall, such as an arteriotomy. In particular, the closure device 200 includes a distal portion 200A and a proximal portion 200B. A biasing member 210, such as spring arms, are configured to provide a motive force to establish relative rotation between the distal portion 200A and the proximal portion 200B. Relative rotation between the distal portion 200A and the proximal portion 200B allows the distal portion 200A to engage a body lumen wall to establish hemostasis relative to a flow of fluid through a puncture in the body lumen wall.

Figure 2B:
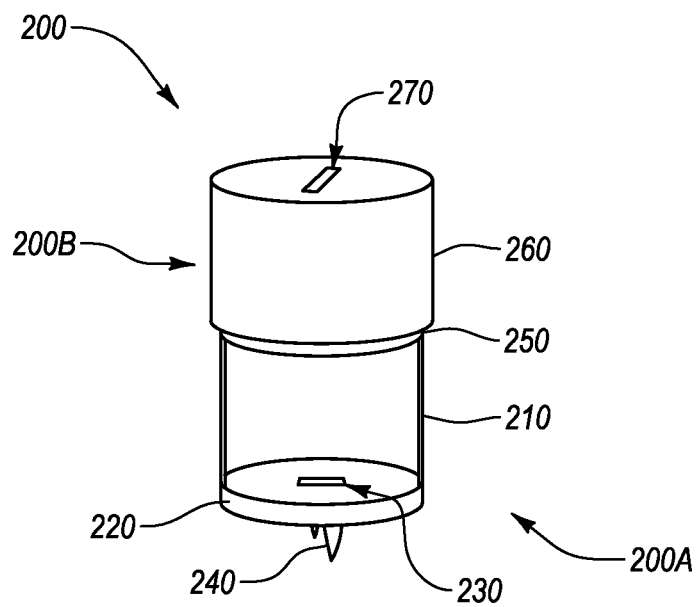
FIG. 2B illustrates a device for closing a puncture in a body lumen wall in a second state according to one example.

For ease of reference, the closure device 200 will be described as moving between a first, pre-deployed state shown in FIG. 2A and a second, deployed state shown in FIG. 2B. It will be appreciated that the deployed state shown in FIG. 2B is a nominal deployed state and the closure device 200 may be deployed in a state between the nominal deployed state shown and the pre-deployed state. Further, to facilitate clarity in viewing the relative positions of each of the elements in various positions, many of the elements will be shown in FIGS. 2A-3E. It will be appreciated that the deployed state and the pre-deployed state can be reversed such that a deployed state is illustrated in FIG. 2A and a pre-deployed state is illustrated in FIG. 2B.

The spring arms 210 are in a nominal deployed state and as such are at least in a partially unbiased state in FIG. 2B. The spring arms 210 can be deflected to the pre-deployed state illustrated in FIG. 2A. Accordingly, in the pre-deployed state the spring arms 210 exert a force on the distal portion 200A to rotate the distal portion 200A toward the deployed state.

As shown in FIG. 2A, the distal portion 200A generally includes a rotation base 220 coupled to the spring arms 210. The rotation base 220 can have any shape. In at least one example, the rotation base 220 includes a locking feature engagement portion 230. The locking feature engagement portion 230 allows the rotation base 220 to be selectively coupled to a locking feature 350, shown in phantom in FIG. 2A. The locking feature engagement portion 230 can include a slot defined in the rotation base 220 while the locking feature 350 can be shaped to be at least partially received within the locking feature engagement portion 230. Tissue engagement features 240, such as tines, can extend away from the rotation base 220 to allow the distal portion 200A to engage a body lumen wall.

As introduced, the spring arms 210 are configured to provide rotation between the distal portion 200A and the proximal portion 200B. In the illustrated example, the proximal portion 200B can include a support base 250 coupled to the spring arms 210. The support base 250 can provide a relatively stable base for the spring arms 210 to act and apply rotational forces on the distal portion 200A.

The support base 250 can also support a plug 260. The plug 260 can optionally be formed from an expandable material. If the plug 260 is formed from an expandable material, the plug 260 can be configured to expand into contact with a tissue tract. Contact between the plug 260 and the tissue tract can further stabilize the proximal portion 200B to thereby facilitate relative rotation of the distal portion 200A in response to the rotational forces generated by deflection of the spring arms 210 as described above. In at least one example, additional gripping features can be operatively associated with an outer perimeter of the plug 260. Such features can include, without limitation, adhesives, tines having any number of configurations, or any other feature or structure configured to provide or increase engagement between an outer perimeter of the plug 260 and a tissue tract or otherwise aid in providing or increasing relative rotation between the distal portion 200A and the proximal portion 200B. Such features can be active or passive features as desired.

In at least one example, support base 250 and/or the plug 260 can include a recess or slot 270 defined therein that allows the locking feature 350 to pass through the proximal portion 200B to engage the distal portion 200A, such as to engage the locking feature engagement portion 230. Such a configuration can thus allow the locking feature 350 to secure the distal portion 200A in a pre-deployed position relative to the proximal portion 200B. The locking feature 350 can then be withdrawn from engagement with the distal portion 200A to allow the spring arms 210 to rotate the distal portion 200A relative to the proximal portion 200B.

FIG. 2B illustrates the closure device 200 in a deployed state. In such a state, the spring arms 210 have rotated the rotation base 220 as the spring arms 210 return toward the nominal deployed state. As shown in FIG. 2B, rotation of the rotation base 220 results in rotation of the tissue engagement features 240, which can allow the closure device 200 to close a puncture in a body lumen wall.

FIGS. 3A-3E illustrate a method for closing a puncture 300 in a body lumen wall 305. The body lumen wall 305 is associated with a body lumen 310 positioned in tissue 315. In the illustrated example, the body lumen wall 305 is positioned at some depth within the tissue 315, such as through a tract which has been previously cut as part of a medical procedure in which the puncture 300 was also formed.

In at least one example, the closure device 200 can be deployed using a deployment device 330. In particular, the deployment device 330 can include an outer housing 335 that includes a distal portion 335A and a proximal portion 335B. An inner housing 340 is positioned within the outer housing 335 that includes a distal portion 340A and a proximal portion 340B that includes a plunger handle 345. The plunger handle 345 is configured to move the inner housing 340 relative to the outer housing 335.

A locking feature 350 can pass through the inner housing 340. In particular, the locking feature 350 can include a distal portion 350A and a proximal plunger portion 350B. The proximal plunger portion 350B can move the locking feature 350 relative to the inner housing 340 and/or the outer housing 335 to move the distal portion 350A to selectively engage and disengage the closure device 200. In some examples, the locking feature can be integrally formed with the inner housing 340.

Figure 3A:
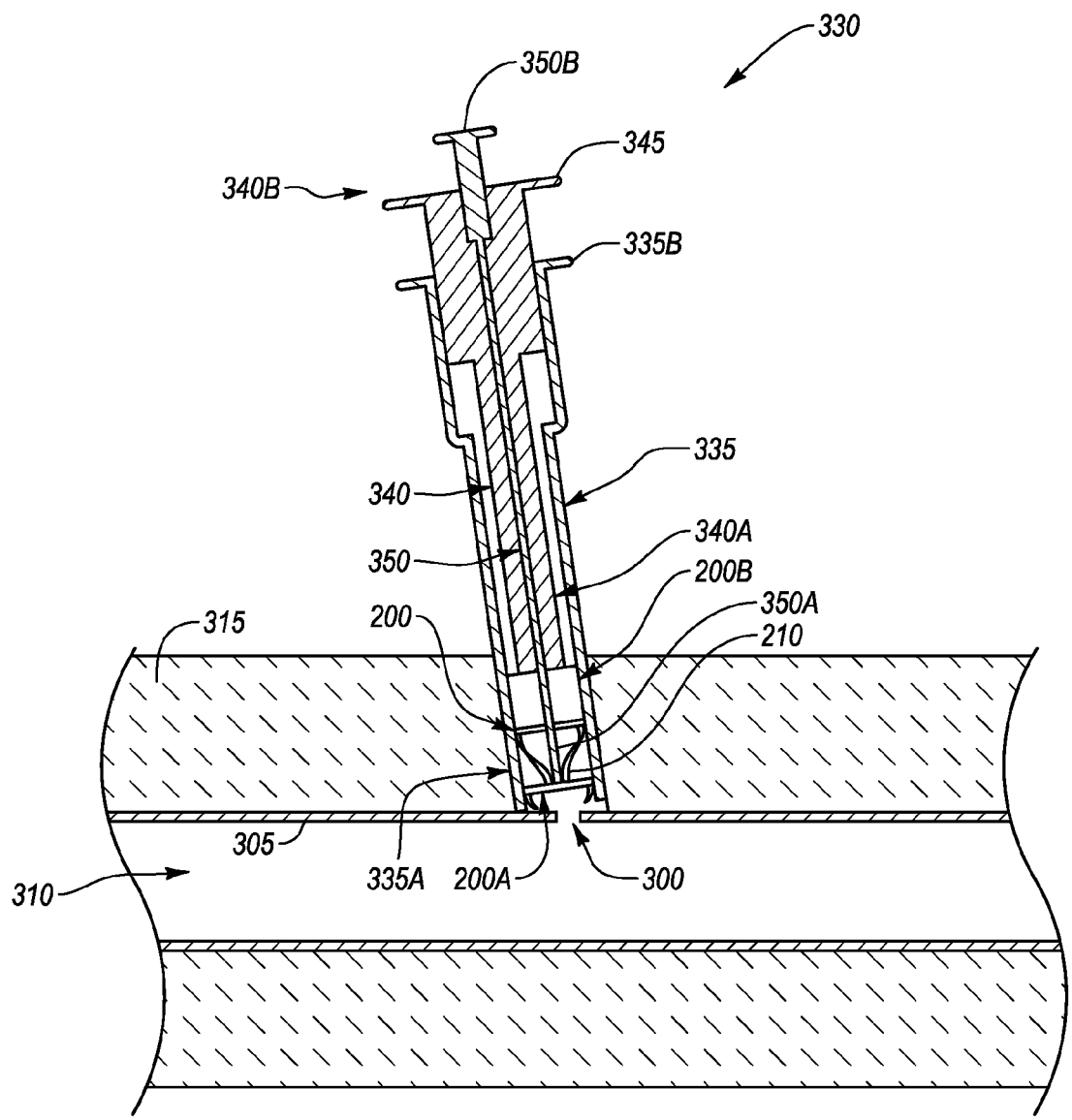
FIGS. 3A-3E illustrate a method for closing a puncture in a body lumen wall according to one example.

As shown in FIG. 3A, the closure device 200 can be positioned within the distal end 335A of the outer housing 335. The closure device 200 can be moved to the pre-deployed position shown in FIG. 3A either before or after the closure device 200 is positioned within the distal end 335A of the outer housing 335.

For example, the closure device 200 can be positioned within the outer housing 335 after which an external device can engage the distal portion 200A of the closure device 200 to rotate the distal portion 200A to the state shown in FIG. 3A. Thereafter, the locking feature 350 can secure the distal portion 200A in the pre-deployed state, as also shown in FIG. 3A, to secure the spring arms 210 in the desired state. For example, the locking feature 350 can be advanced relative to the outer housing 335 to move the distal portion 350A into engagement with the distal portion 200A and with the locking feature engagement portion 230 (FIGS. 2A, 2B). With the closure device 200 positioned within the deployment device 330 and the spring arms 210 secured in the desired state, the distal end 335A of the outer housing 335 can be advanced into proximity with the body lumen wall 305 near the puncture 300.

Figure 3B:
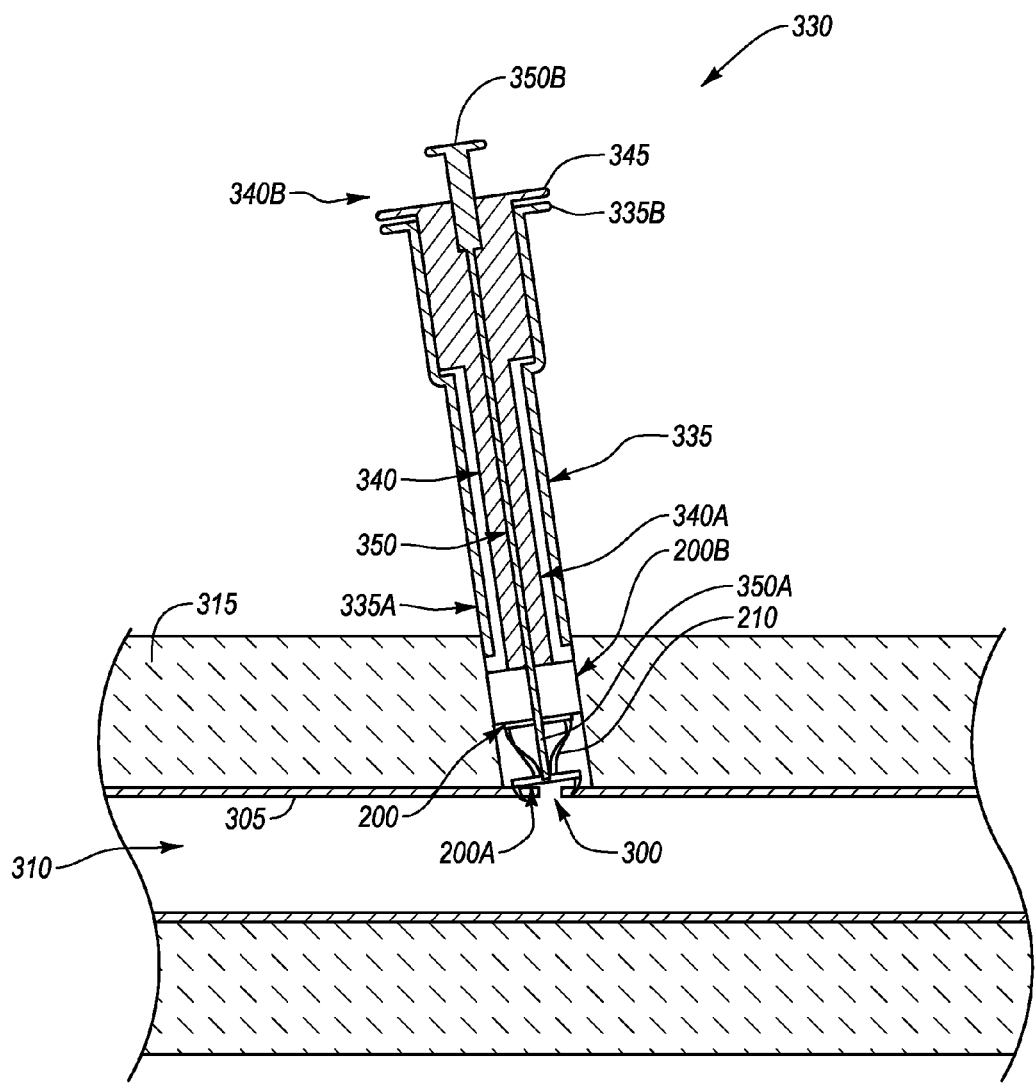
Figure 3C:
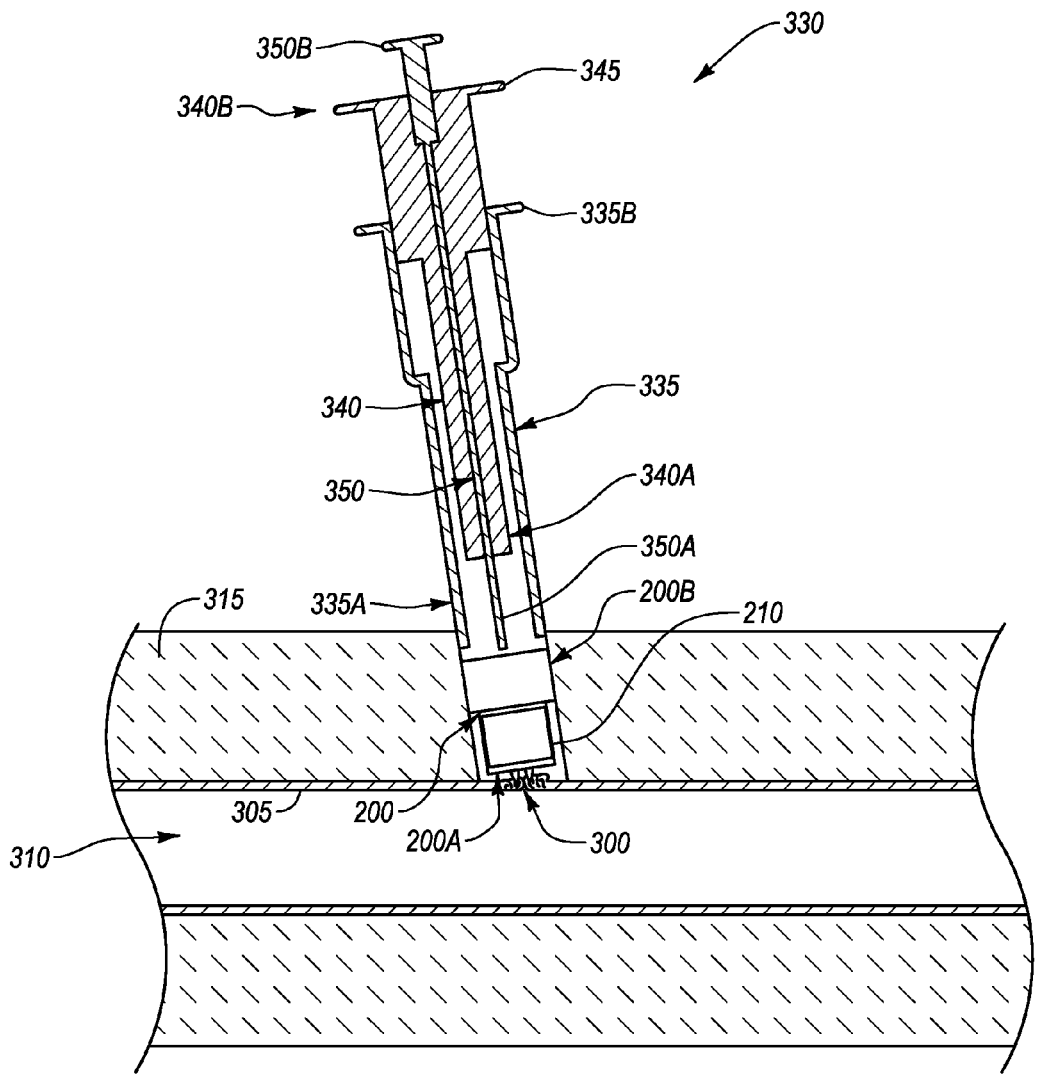

As illustrated in FIG. 3B, the inner housing 340 can be advanced distally relative to the outer housing 335, such as by moving the plunger handle 345 toward proximal end 335B of the outer housing 335. As the plunger handle 345 moves toward the proximal end 335B of the housing 335 thereby moving the distal end 340A of the inner housing 340 distally relative to the distal end 335A of the outer housing 335.

As the distal end 340A of the inner housing 340 moves distally relative the outer housing 335, the distal end 340A engages the proximal end 200B of the closure device 200 to thereby move the closure device 200 from the distal end 335A of the outer housing 335. In at least one example, as the proximal portion 200B is moved from the distal end 335A of the outer housing 335, the plug 260 associated with the proximal portion 200B can expand into contact with the tissue 315. Further, as the closure device 200 is urged from the distal end 335A of the housing, the tissue-engagement features 240 can engage the body lumen wall 305. In at least one example, the locking feature 350 can advance with inner housing 340 relative to the outer housing 335. Such a configuration can allow the locking feature 350 to remain in engagement with the distal portion 200A of the closure device 200.

Thereafter, the locking feature 350 can be drawn proximally relative to the outer housing 335. As the locking feature 350 is drawn proximally, the distal end 350A of the locking feature 350 disengages from the distal portion 200A of the closure device 200. As the locking feature 350 disengages the distal portion 200A, the spring arms 210 move the distal portion 200A toward the deployed position, thereby rotating the distal portion 200A. As the spring arms 210 rotate the distal portion 200A, the tissue engagement features 240 also rotate.

Figure 3D:
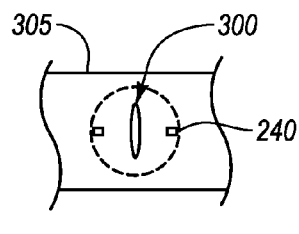
Figure 3E:
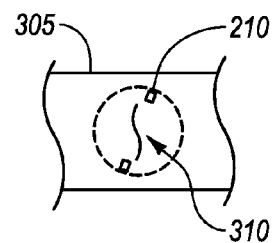

As previously introduced and as shown in FIG. 3D, the tissue engagement features 240 are in engagement with the body lumen wall 305. In at least one example, the tissue engagement features 240 can engage the body lumen wall 305 on opposing sides of the puncture 300. The tissue engagement features 240 rotate to the position shown in FIG. 3E in response to the rotation of the distal portion 200A caused by the spring arms 210. As the tissue engagement features 240 rotate, they can also twist the body lumen wall 305 to thereby close the puncture 300. Accordingly, the closure device include two portions configured such that relative rotation between the two after the device is in position near a body lumen wall can provide hemostasis for a puncture in the body lumen wall.

Figure 4A:
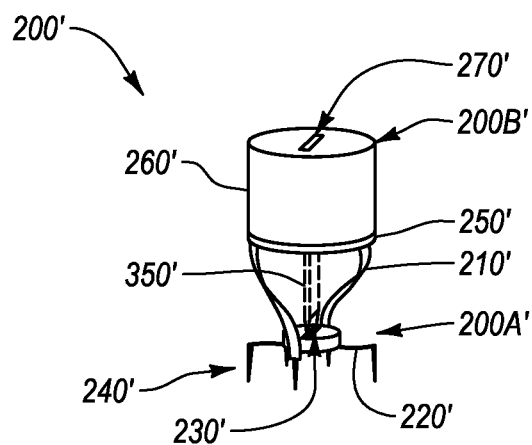
FIGS. 4A-4B illustrate a device for closing a puncture in a body lumen wall according to one example.
Figure 4B:
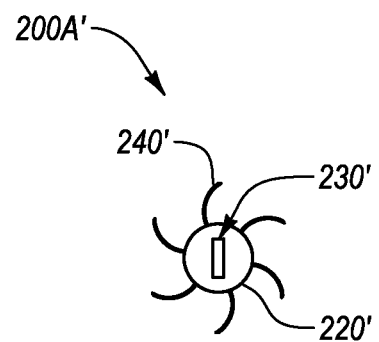

In FIGS. 2A-2C and 3A-3E the closure device 200 shown includes a pair of opposing tissue engagement portions 240. It will be appreciated that other configurations are possible. For example, FIGS. 4A-4B illustrate a closure device 200' having a distal portion 200A' and a proximal portion 200B' as well as tissue engagement portions 240' that are arranged in a pinwheel configuration. In particular, FIG. 4A illustrates a perspective view of the closure device 200' while FIG. 4B illustrates the distal portion 200A' in more detail. Accordingly, the tissue engagement portions can have a variety of configurations. The closure device 200' includes a distal portion 200A' and a proximal portion 200B'. A spring, such as spring arms 210' are configured to provide a motive force to move established relative rotation between the distal portion 200A' and the proximal portion 200B'.

The distal portion 200A' generally includes a rotation base 220' coupled to the spring arms 210'. The rotation base 220' can have any shape. In at least one example, the rotation base 220' includes a locking feature engagement portion 230'. The locking feature engagement portion 230' allows the rotation base 220' to be selectively coupled to a locking feature 350', shown in phantom in FIG. 2A. The locking feature engagement portion 230' can include a slot defined in the rotation base 220' while the locking feature 350' can be shaped to be at least partially received within the locking feature engagement portion 230'. Tissue engagement features 240', such as tines, can extend away from the rotation base 220' to allow the distal portion 200A' to engage a body lumen wall.

The proximal portion 200B' can include a support base 250' coupled to the spring arms 210'. In at least one example, support base 250' and/or a plug 260' can include a recess or slot 270' defined therein that allows the locking feature 350' to pass through the proximal portion 200B to engage the distal portion 200A. The shape and/or size of the slot 270' can allow the locking feature 350' to engage the locking feature engagement portion 230' while allowing the locking feature 350' to rotate within the proximal portion 200B'.

Figure 5A:
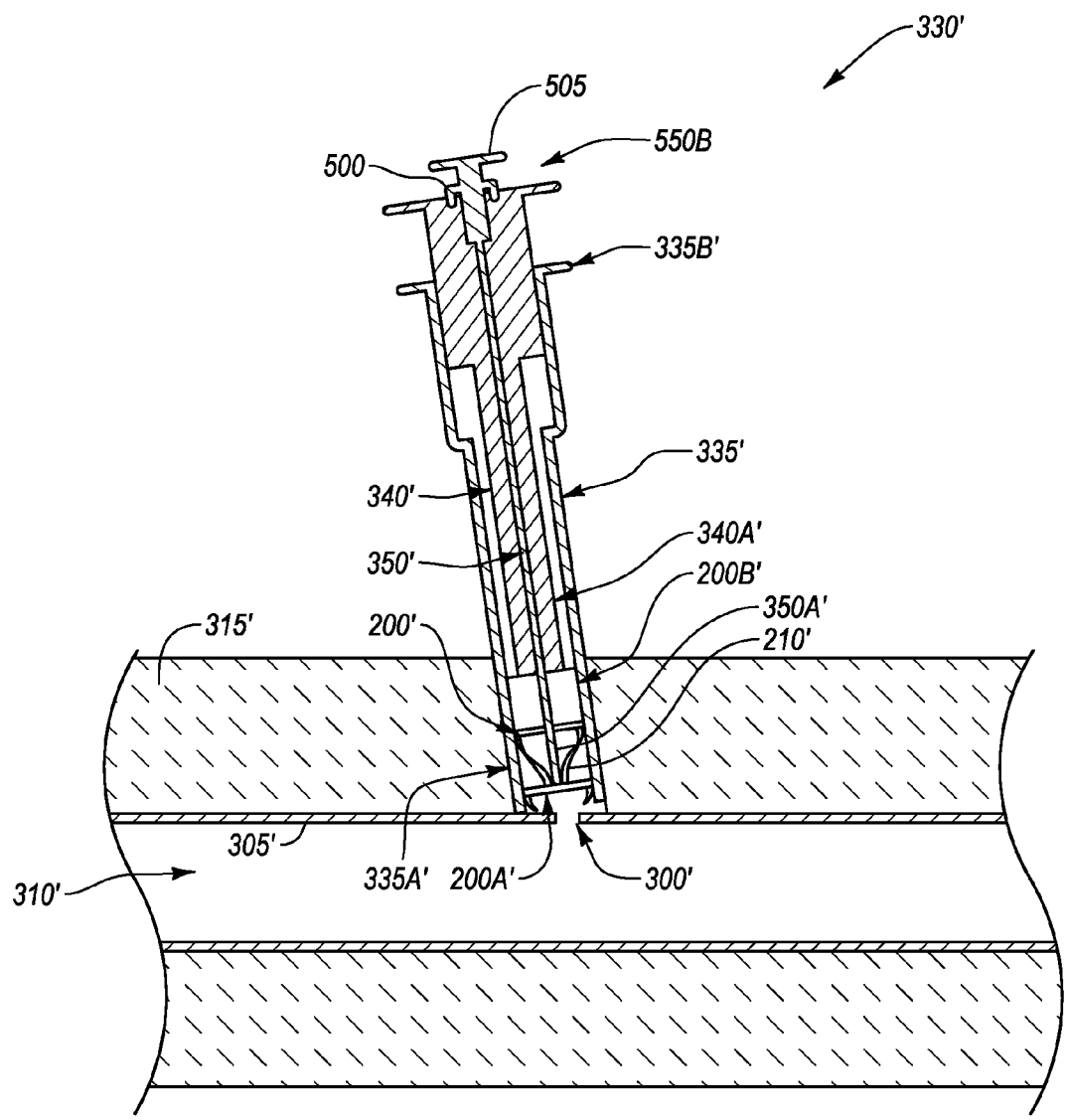
FIGS. 5A-5C illustrate a method for closing a puncture in a body lumen wall according to one example.
Figure 5B:
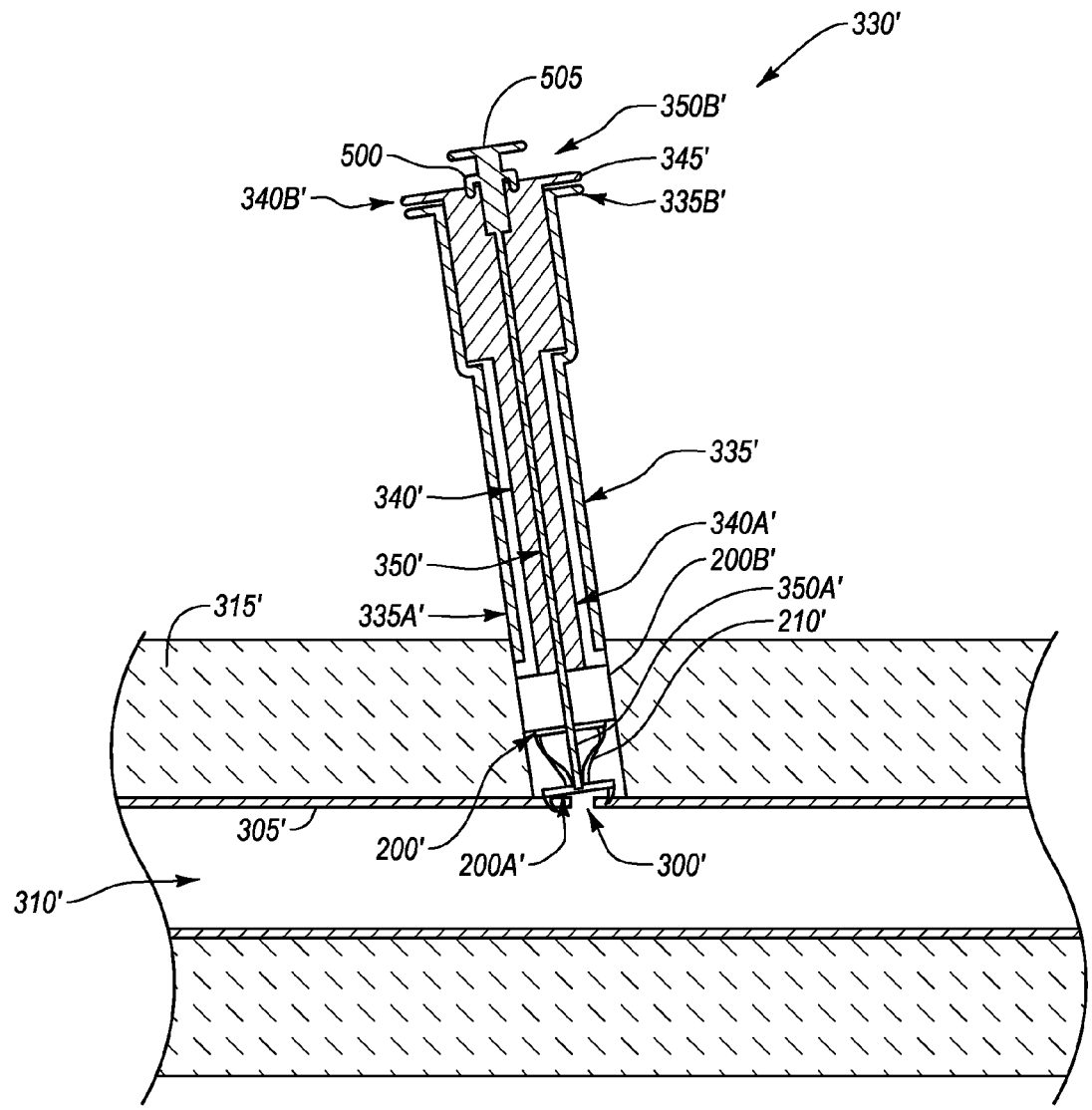
Figure 5C:
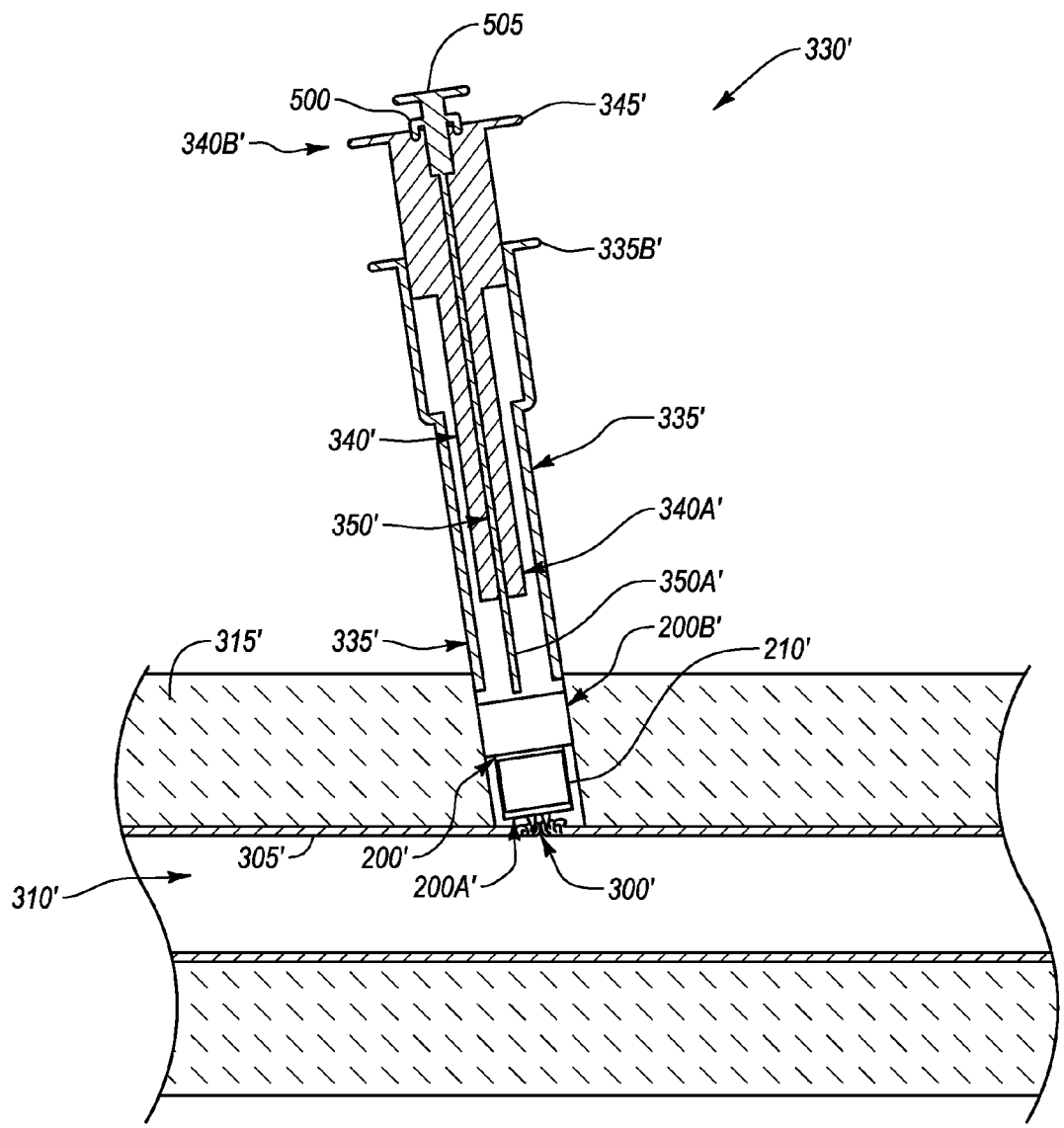

FIGS. 5A-5C illustrate the closure device 200' positioned within a deployment device 330' to close a puncture 300 in a body lumen wall 305. The deployment device 330' is configured to move the closure device 200' to the pre-deployed state. In particular, as illustrated in FIG. 5A, the deployment device 330 can include a locking feature 350' that includes a distal end 350A' configured to engage a distal end 200A' of the closure device.

The deployment device 330' can include an outer housing 335' that includes a distal portion 335A' and a proximal portion 335B'. An inner housing 340' is positioned within the outer housing 335' that includes a distal portion 340A' and a proximal portion 340B' that includes a plunger handle 345'.

A locking feature 350' can pass through the inner housing 340'. In particular, the locking feature 350' can include a distal portion 350A' and a proximal portion 350B'. The proximal portion 350B' can include an engagement feature 500 configured to selectively engage a corresponding feature on a distal portion of the deployment device 330', such as on a proximal portion 340B' of the inner housing 340'. The proximal portion 350B' of the locking feature 350' can also include a plunger handle 505 that translates and rotates with the engagement feature 500. In at least one example, the plunger can move the locking feature 350' relative to the inner housing 340' and/or the outer housing 335' to move the distal portion 350A' to selectively engage and disengage the closure device 200'.

As shown in FIG. 5A, the closure device 200' can be positioned within the distal end 335A' of the outer housing 335'. The locking feature 350' can move the distal portion 200A' to a pre-deployed state and to lock the distal portion 200' in the pre-deployed state. For example, once the closure device 200' is positioned within the distal end 335A' of the outer housing 335', the plunger handle 505 can advance the locking feature 350' into engagement with the distal portion 200A' of the closure device 200'.

The engagement feature 500 and the plunger handle 505 can then be rotated relative to at least the outer housing 335' to rotate the distal portion 200A' relative to the proximal portion 200B' and thus move or bias the closure device 200' to the pre-deployed state. The engagement feature 500 can then be secured to a corresponding portion of the inner housing 340' to maintain the closure device 200' in the pre-deployed state.

The interaction between the engagement feature 500 and the inner housing 340' can be any type of interaction that allows the locking feature 350' to move the closure device 200' to the pre-deployed state and to maintain the closure device 200' at that state. For example, a tab and detent interaction can be provided as in FIG. 5A. Further, ratcheting interaction as well as any other type of coupling can be used to provide the functionality described above.

Accordingly, in at least one example the proximal end 350B' of the locking feature 350' can be used to move the closure device 200' to a pre-deployed state and/or to maintain the closure device 200' at that state. With the closure device 200' in the pre-deployed state, the distal end 335A' of the outer housing 335' can be positioned in proximity to the body lumen wall 305 as shown in FIG. 5A.

Thereafter, as shown in FIG. 5B, the inner housing 340' can be moved distally relative to the outer housing 335'. As the inner housing 340' moves distally relative to the outer housing 335', the distal end 340A' can contact the proximal portion 200B' of the closure device 200' to thereby urge the closure device 200' from the distal end 335A' of the outer housing 335'. In at least one example, the locking feature 350' moves with the inner housing 340'. Further, as the closure device 200' is urged from the distal end 335A' of the housing, the tissue-engagement features 240' (FIG. 4A) can engage the body lumen wall 305.

Thereafter, the locking feature 350' can be disengaged from the inner housing 340' to allow the closure device 200' to move to the deployed state as shown in FIG. 5C to close the puncture 300 in the body lumen wall 305. In particular, the engagement feature 500 of the locking feature 350' can be drawn proximally to disengage the locking feature 350' from the corresponding portion of the inner housing 340'. The locking feature can be further drawn proximally relative to the inner housing 340' and the outer housing 335' to free the locking feature 350' from the closure device 200'. Engagement between the tissue engagement features 240' (FIG. 4A) and the body lumen wall 305 closes the puncture 300, as described above. Accordingly, the closure device 200' is configured to establish hemostasis for the puncture 300 in the body lumen wall 305 by providing relative rotation between the distal portion 200A' and the proximal portion 200B'.

Figure 6A:
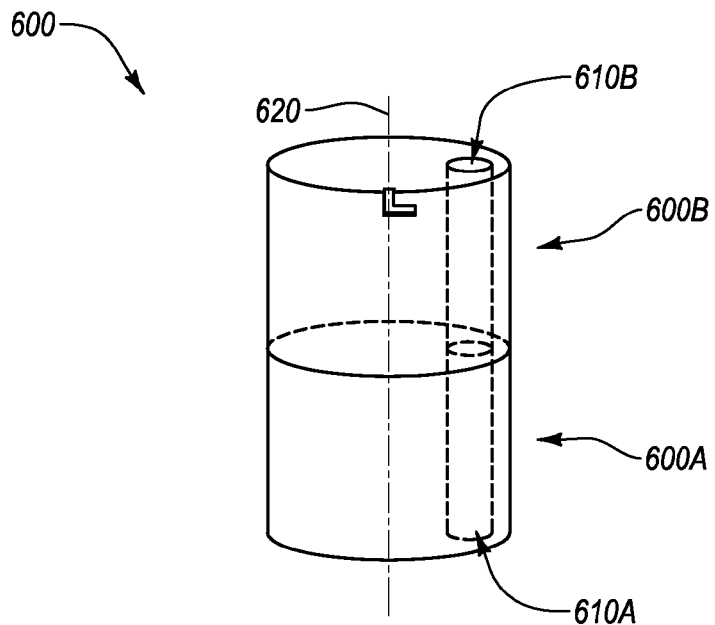
FIG. 6A illustrates a device for closing a puncture in a body lumen wall in a first state according to one example.
Figure 6B:
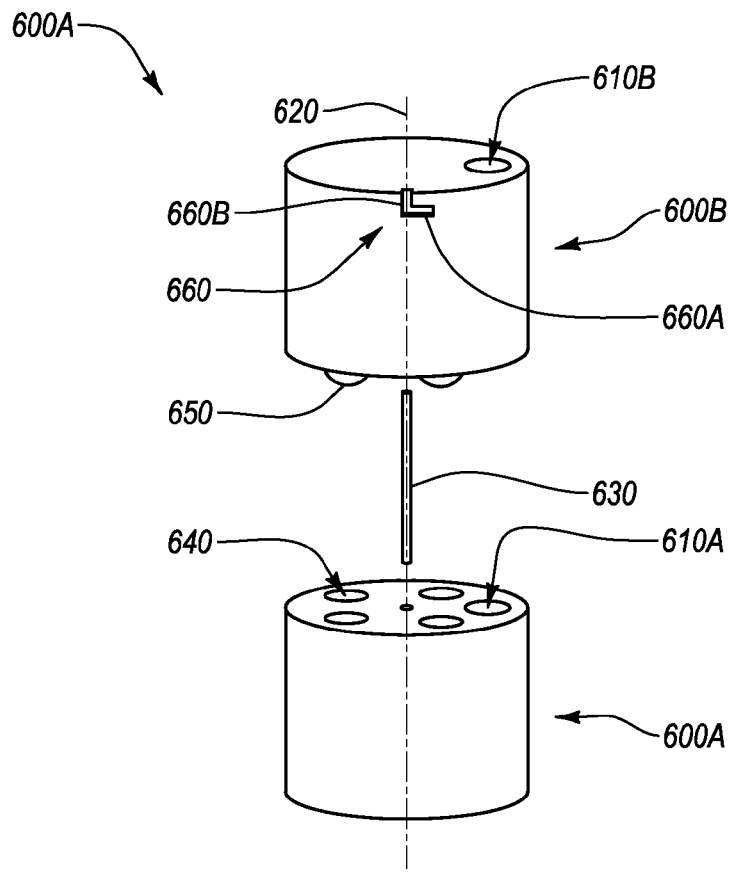
FIG. 6B illustrates an exploded view of the device for closing a puncture of FIG. 6A.
Figure 6C:
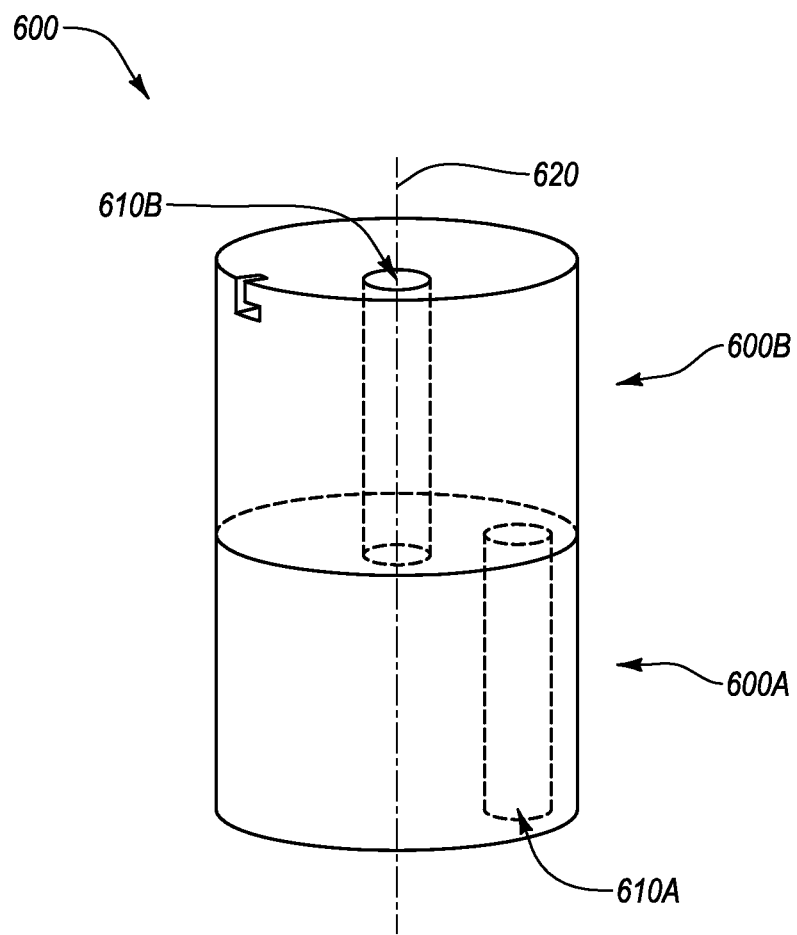
FIG. 6C illustrates the device for closing a puncture in a body lumen wall shown in FIG. 6A in a second state.

FIGS. 6A-6C illustrate a closure device 600 that includes a distal portion 600A and a proximal portion 600B. Relative rotation between the distal portion 600A and the proximal portion 600B establishes hemostasis for a puncture in a body lumen wall. FIG. 6A illustrates an assembled view of the closure device 600 in a first state, FIG. 6B illustrates an exploded view of the closure device 600, and FIG. 6C illustrates the closure device 600 in a second state. As will be discussed in more detail below, the closure device 600 can be moved between the first state and the second state as desired to provide access to a body lumen through a puncture in a body lumen wall and to establish hemostasis for the puncture.

Referring to FIG. 6A, the distal portion 600A includes a distal access port 610A defined therein while the proximal portion 600B includes a proximal access port 610B defined therein. The distal access port 610A and the proximal access port 610B can each be offset relative to a central axis 620 of the closure device 600. Such a configuration can allow the distal access port 610A and the proximal access port 610B to be aligned to provide an opening that passes through the closure device 600, as shown in FIG. 6A. Further, the closure device 600 is configured to allow relative rotation between the proximal portion 600B and the distal portion 600A.

As illustrated in FIG. 6B the distal portion 600A and the proximal portion 600B can include and be coupled by a pin 630 positioned along the central axis 620. Such a configuration can allow the distal portion 600A and the 600B to rotate about the pin 630 and thus along the central axis 620.

The closure device 600 can also be configured to help maintain the distal portion 600A and the proximal portion 600B in desired states. For example, the distal portion 600A and the proximal portion 600B can include tab and detent features. In the illustrated example tabs 640 can be associated with the proximal portion 600B while corresponding detents 650 can be associated with the distal portion 600A. The interaction between the tabs 640 and the detents 650 can help reduce unintended rotation. It will be appreciated that tabs and/or detents can be positioned on either or both of the distal portion 600A and the proximal portion 600B. Further, while the pin 630 is illustrated as a separate component, it will be appreciated that the pin 630 can be integrated with either the distal portion 600A or the proximal portion 600B. Alternatively, the pin 630 can be omitted entirely.

In addition to tabs 640 and detents 640, unintended rotation can be achieved by other manners. A friction fit between the distal portion 600A and the proximal portion 600B can prevent unwanted rotations while permitting desired rotations when sufficient torque is applied. In other embodiments, the interaction between the distal portion 600A and the proximal portion 600B may have a tooth engagement such as a ratchet engagement such that rotation of the proximal portion 600B in one direction only is permitted. This type of ratchet engagement may also include a stop such to prevent the ports 610A and 610B from realigning after deployment or to prevent 360 degrees of rotation.

In at least one example, the proximal portion 600B can include guide channels 660 defined therein. Each guide channel 660 can include a distal portion 660A and a proximal portion 660B in communication with the distal portion 660A. The proximal portion 660B can be sized to receive a rotational member to and to allow the rotational member to be moved into and out of engagement with the distal portion 660A. The distal portion 660A of the guide channel 660 is configured to allow a rotational member to rotate the proximal portion 660B relative to the distal portion 660A to thereby move the closure device 600 to the second state shown in FIG. 6C.

It can be appreciated that the guide channels 660 can be located on the side of the proximal portion 600B or on a top surface of the proximal portion 600B. The guide channels can further be shaped, in some embodiments, to permit engagement with a deployment device in a manner that permits the deployment device to rotate the proximal portion 600B relative to the distal portion 600A. Polygonal shapes, indentations, multiple indentations, and the like. The rotational member can engage with the guide members to rotate to multiple positions.

In the second state shown in FIG. 6C, the proximal access port 610B is moved out of alignment with the distal access port 610A. In such a state, the proximal access port 610B is in communication with a non-ported portion of the distal portion 600A while the distal access port 610A is in communication with a non-ported portion of the proximal portion 600B. Accordingly, a flow of fluid directed to the distal access port 610A will be blocked by the proximal portion 600B. Such a configuration in turn can allow the closure device to provide hemostasis to block the flow of fluid from a puncture body lumen wall, as will now be discussed.

FIGS. 7A-7E illustrate a method of establishing hemostasis relative to a puncture 300 in a body lumen wall 305. The method can include positioning a closure device 300 in a deployment device 700. The deployment device 700 can generally include an outer housing 710 having a distal end 710A and a proximal end 710B. The deployment device 700 further includes an inner housing 720 having a distal end 720A and a proximal end 720B configured to translate within the inner housing 710.

In at least one example, the proximal end 720B of the inner housing 720 includes a rotation feature 730 configured to engage the guide channels 660 (FIGS. 6A-6C). Such a configuration can allow the rotation feature 730 to engage the closure device 600 and draw the closure device 600 proximally into the distal end 710A of the outer housing 710. As previously described, the rotational feature 730 can be configured to engage the closure device 600 on sides of the device 600, on a top surface of the device 600, and the like.

Figure 7A:
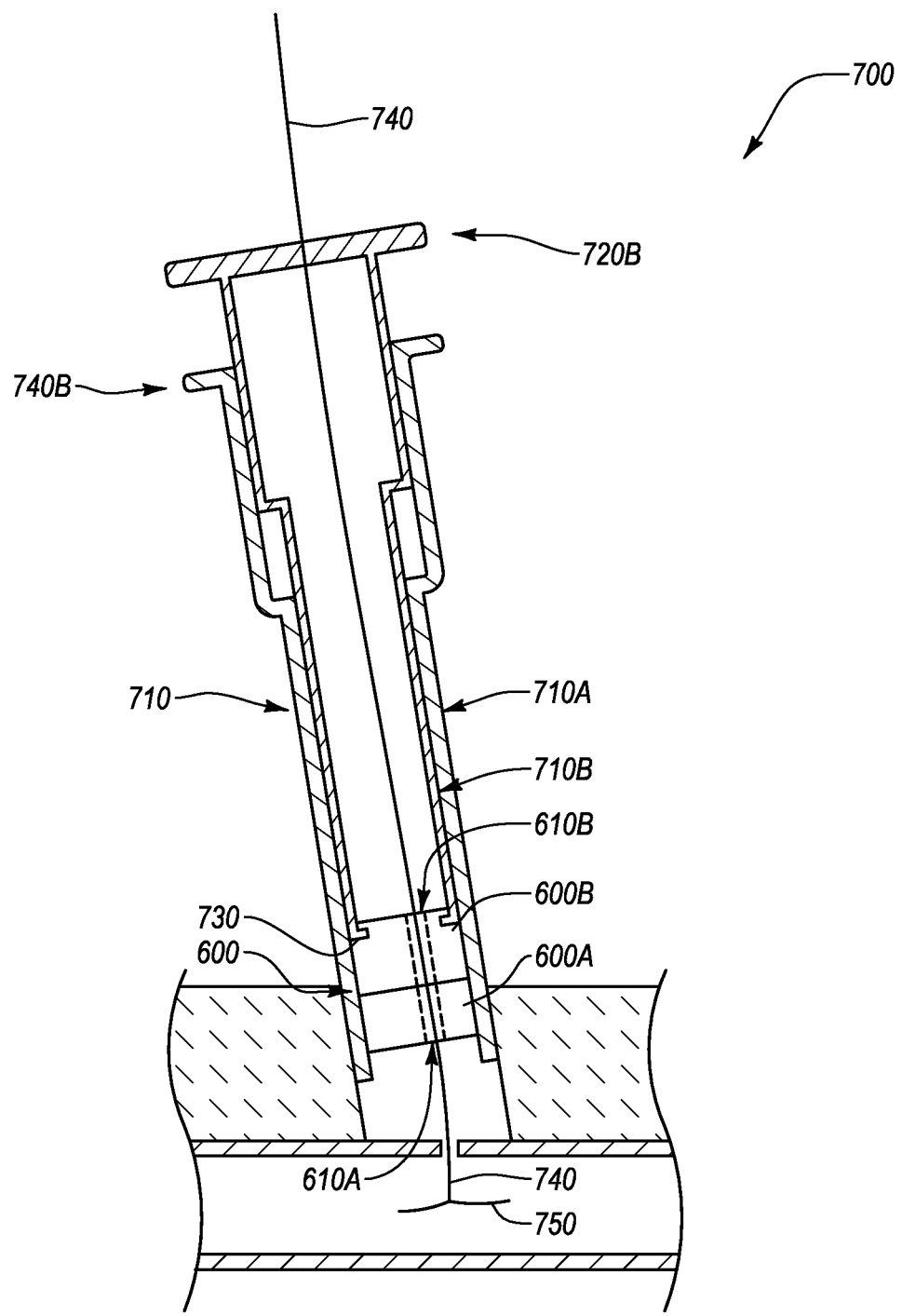
FIGS. 7A-7E illustrate a method for closing a puncture in a body lumen wall according to one example.

Once the closure device 600 is thus positioned within the deployment device 700, the distal end 710A of the outer housing 710 can be positioned within a tract in tissue 315 near the body lumen wall 305 as shown in FIG. 7A. The distal access port 610A and the proximal access port 610B can then be aligned, if not already aligned. Thereafter, a guide wire 740 having a distal expandable foot 750 can be passed through the closure device 600 by way of the proximal access port 610B and the proximal access port 610A. The guide wire 740 can then be passed through the puncture 300 and into the body lumen 310 to thereby position the expandable foot 750 distally of the body lumen wall 305. In at least one example, a sheath or other device (not shown) can be included with the guide wire 740 to selectively expand and retract the expandable foot 750.

The expandable foot 750 can then be expanded and drawn into contact with the body lumen wall 305 by drawing the guide wire 740 proximally. The deployment device 700 can then be urged into proximity with the body lumen wall 305 by maintaining tension of the guide wire 740 to provide a relatively stationary base from which a desired force can be applied to advance the deployment device 700 relative to tissue 315 toward the body lumen wall 305.

Figure 7B:
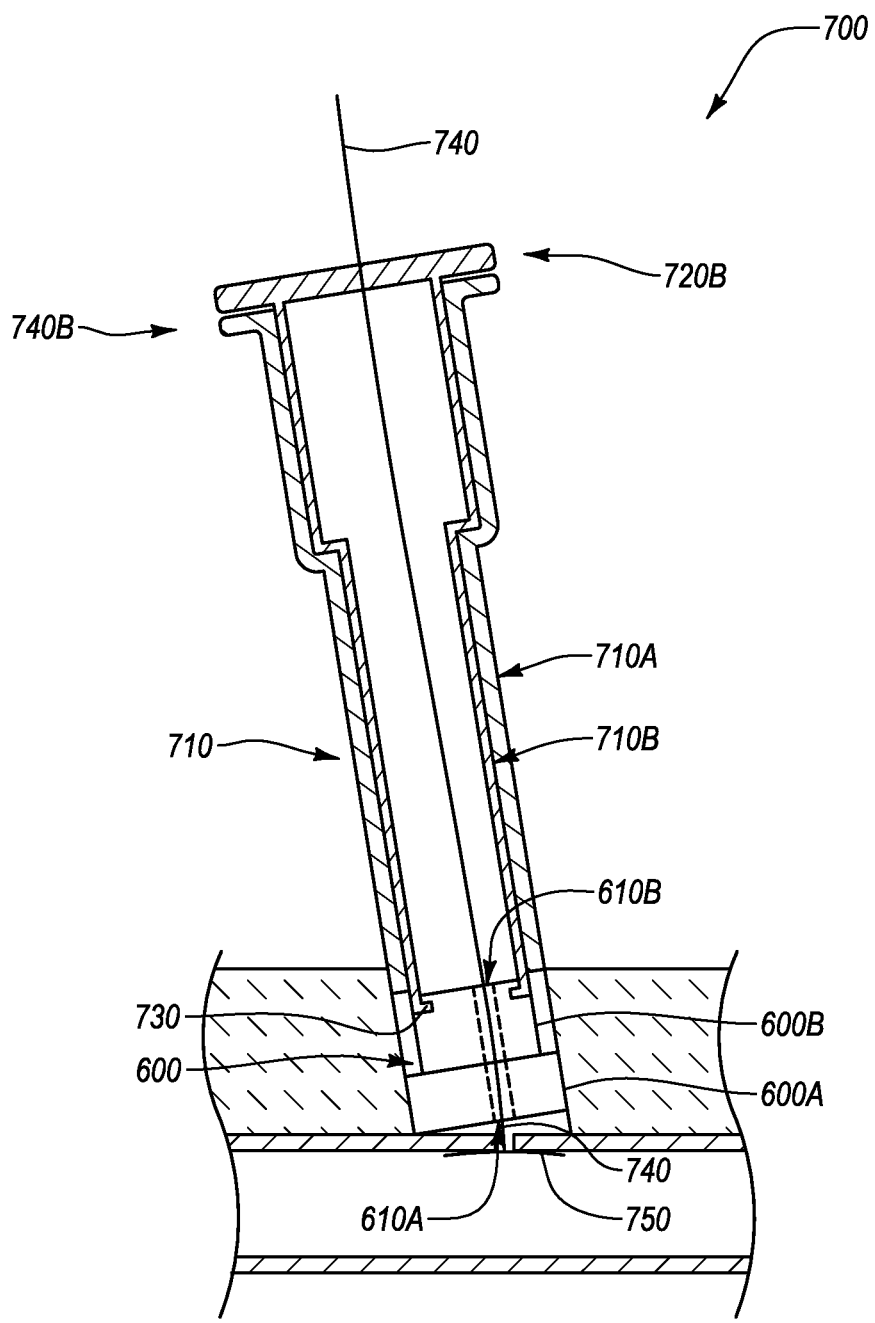

Thereafter, as shown in FIG. 7B, the inner housing 720 can be advanced distally relative to the outer housing 710 to thereby cause the distal end 720A of the inner housing 720 to urge the closure device 600 from the distal end 710A of the outer housing 710. In at least one example, portions of the distal portion 600A and/or the proximal portion 600B can be formed of an expandable material.

In such an example, the expandable material can expand as it is urged from the distal end 710A of the outer housing 710 to thereby establish contact with the corresponding portion of the closure device 600 and the adjacent tissue 315. The contact can be sufficient to provide a seal between the closure device 600 and the tissue 315 and/or to provide sufficient contact to allow relative rotation between the distal portion 600A and the proximal portion 600B of the closure device 600.

Figure 7C:
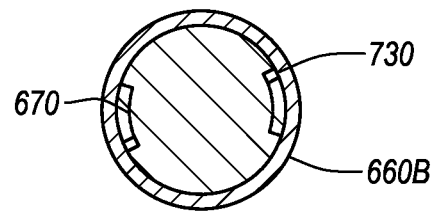

Once the closure device 600 is in position relative to the body lumen wall 305, the collapsible foot 750 can be collapsed and the collapsible foot 750 and the guide wire 740 can be withdrawn through the closure device 600 as shown in FIG. 7C. Once the collapsible foot 750 and the guide wire 740 are withdrawn through the closure device 600, the inner housing 720 can be rotated relative to the outer housing 710. As the inner housing 720 rotates, the rotation features 730 engage the proximal portion 600B adjacent the guide channels 660.

In particular, FIG. 7C illustrates the engagement between the distal portion 660A of the guide channel (FIGS. 6A-6C) and the rotation feature 730. As illustrated in FIG. 7C, the rotation feature 730 can extend inwardly from the inner housing 720 into the distal portion 660A of the guide channel (FIGS. 6A-6C). As previously introduced, the rotation feature 730 can be moved into engagement with the distal portion 660A by way of the proximal portion 660B (FIGS. 6A-6C). Thereafter, as the rotation feature 730 rotates in the direction shown the rotation feature 730 can come into contact with a shoulder portion 670 of the proximal portion 600A adjacent the distal portion 660A of the guide channel 660 (FIGS. 6A-6C).

Figure 7D:
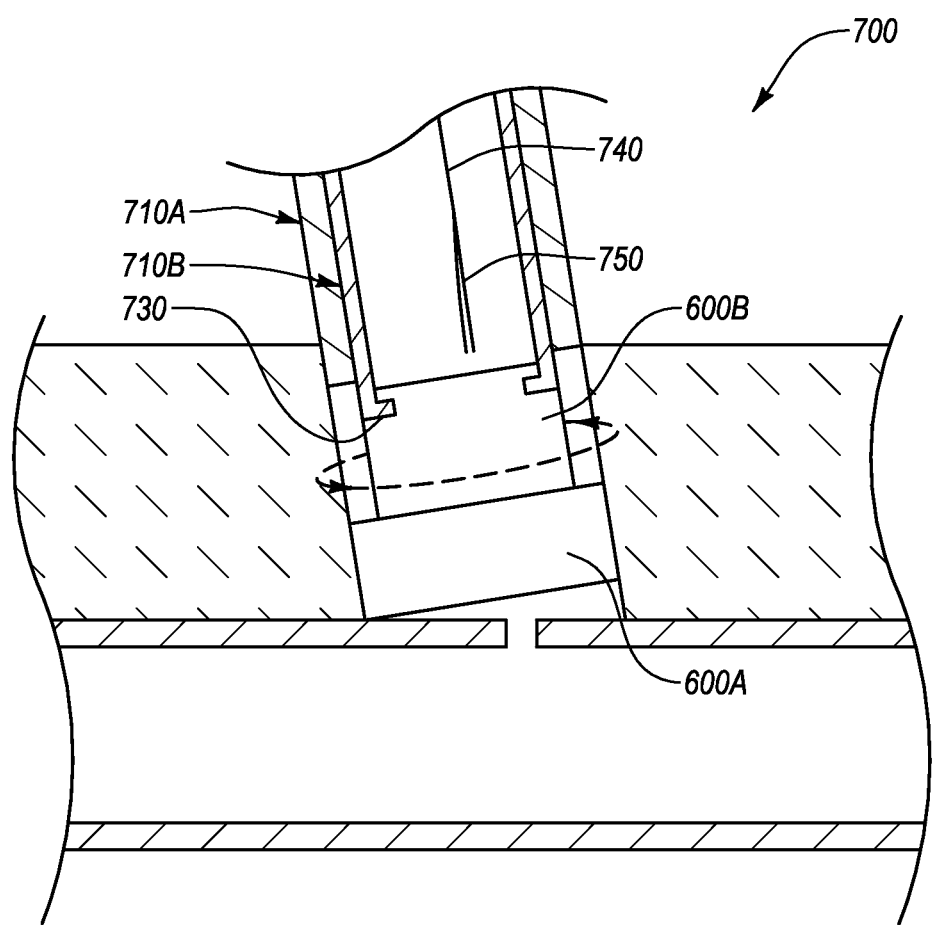
Figure 7E:
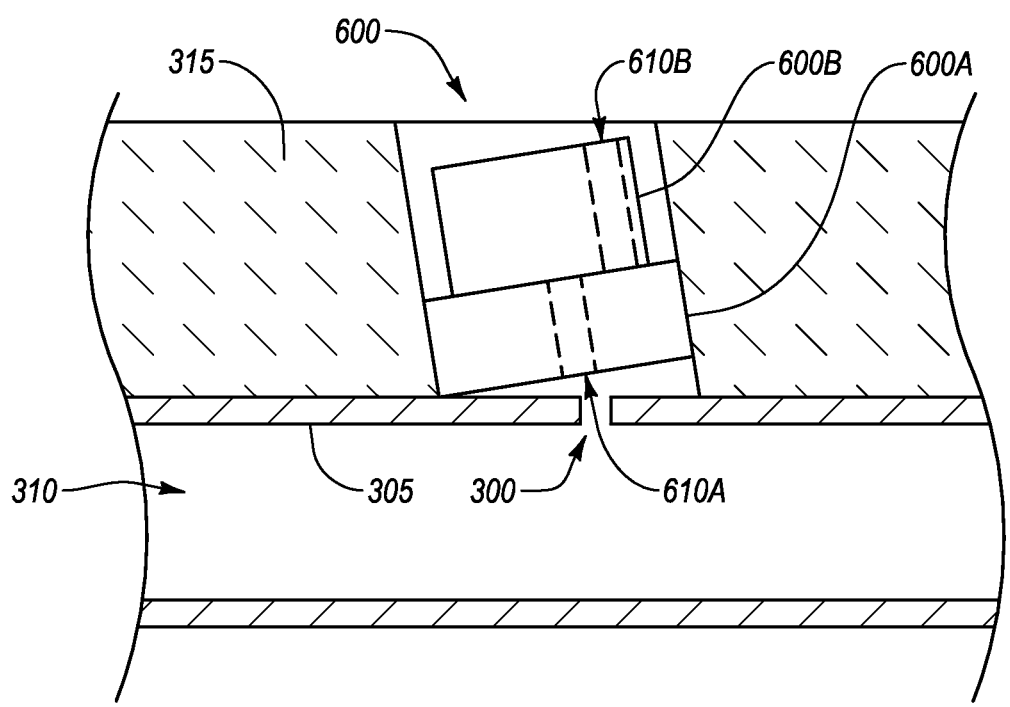

Contact between the rotation feature 730 and the shoulder portion 670 can cause the proximal portion 600B of the closure device 600 to rotate relative to the distal portion 600A as illustrated in FIG. 7D. As shown in 7E, rotation of the proximal portion 600B moves the proximal access port 610B out of communication with the distal access port 610A, thereby preventing the flow of fluid from the puncture 305 through the closure device 600. Accordingly, relative rotation between the proximal portion 600B and the distal portion 600 can help establish hemostasis relative to the flow of fluid from the puncture 300. Consequently, closure devices can include various configurations in which relative rotation between a distal portion and a proximal portion establishes hemostasis relative to a puncture in a body lumen wall.

In one embodiment, the bio-absorbable or bio-degradable distal portion of the device such as the closure device 600, is pulled into the puncture in the vessel or lumen wall. This can be performed by applying sufficient tension to the guide wire as described herein until the distal portion is positioned in the puncture. Once the distal portion has plugged the puncture, the guide wire is removed and the proximal portion of the closure device is rotated to establish hemostasis.

The invention is susceptible to various modifications and alternative means, and specific examples thereof have been shown by way of example in the drawings and are herein described in detail. It should be understood, however, that the invention is not to be limited to the particular devices or methods disclosed, but to the contrary; the invention is to cover all modifications, equivalents, and alternatives falling within the spirit and scope of the claims.

What is claimed is:

1. A method of establishing hemostasis relative to a puncture in a body lumen wall, comprising:
    positioning a closure device in a distal end of a deployment device;
    positioning the closure device in a tissue tract in proximity with the puncture in the body lumen wall with the deployment device, the closure device including a distal portion and a proximal portion, the closure device including a central longitudinal axis and a biasing member coupling the proximal portion and the distal portion;
    moving tissue engagement features associated with the distal portion into engagement with a proximal surface of the body lumen wall;
    after moving the tissue engagement features associated with the distal portion into engagement with the proximal surface of the body lumen wall, actuating the deployment device to establish relative rotation between the distal portion and the proximal portion of the closure device about the central longitudinal axis to establish hemostasis relative to the puncture, the actuating the deployment device including releasing the biasing member to allow the biasing member to move from a pre-deployed state to a deployed state; and
    deploying the closure device.

2. The method of claim 1, wherein actuating the deployment device to establish relative rotation between the distal portion and the proximal portion causes the tissue engagement features to rotate while in engagement with the body lumen wall to close the puncture.

3. The method of claim 2, wherein the tissue engagement features include tines and wherein moving tissue engagement features associated with the distal portion into engagement with the body lumen wall includes moving tines into engagement with the body lumen wall.

4. The method of claim 3, wherein moving tine into engagement with the body lumen wall includes moving tines arranged in a pinwheel pattern into engagement with the body lumen wall.

5. The method of claim 1, wherein releasing the biasing member to allow the biasing member to move from a pre-deployed state to a deployed state includes removing a locking feature associated with the deployment device from engagement with a locking feature engagement portion associated with the distal portion.

6. The method of claim 1, wherein actuating the deployment device to establish relative rotation between the distal portion and the proximal portion includes engaging the proximal portion with a rotation feature associated with the deployment device and rotating the rotation feature relative to the distal portion of the closure device.

7. The method of claim 6, wherein rotating the rotation feature relative to the distal portion of the closure device rotates a proximal access port defined in the proximal portion relative to a distal access port defined in the distal portion.

8. The method of claim 6, further including expanding at least one of the distal portion or the proximal portion into engagement with the tissue tract.

9. The method of claim 8, the tissue tract defining a lumen with an interior surface and wherein the proximal portion engages the interior surface of the lumen of the tissue tract.

10. A method of establishing hemostasis relative to a puncture in a body lumen wall, comprising:
  positioning a closure device in a distal end of a deployment device;
  positioning the closure device in a tissue tract in proximity with the puncture in the body lumen wall with the deployment device, the closure device including a distal portion, and a proximal portion, the closure device including a biasing member that couples the distal portion and the proximal portion and a central longitudinal axis extending through the distal portion and the proximal portion;
  actuating the deployment device to deploy the closure device and release the biasing member to allow the biasing member to move from a pre-deployed state to a deployed state and establish relative rotation between the distal portion and the proximal portion of the closure device about the central longitudinal axis to establish hemostasis relative to the puncture, actuating the deployment device including engaging the proximal portion with a rotation feature associated with the deployment device and rotating the rotation feature relative to the distal portion of the closure device; and
  deploying the closure device.

11. The method of claim 10, further comprising moving a plurality of tissue engagement features associated with the distal portion into engagement with the body lumen wall and wherein actuating the deployment device to establish relative rotation between the distal portion and the proximal portion causes the tissue engagement features to rotate while in engagement with the body lumen wall to close the puncture.

12. The method of claim 11, wherein the plurality of tissue engagement features include tines and wherein moving tissue engagement features associated with the distal portion into engagement with the body lumen wall includes moving tines into engagement with the body lumen wall.

13. The method of claim 10, wherein releasing the biasing member to allow the biasing member to move from a pre-deployed state to a deployed state includes removing a locking feature associated with the deployment device from engagement with a locking feature engagement portion associated with the distal portion.

14. The method of claim 10, wherein rotating the rotation feature relative to the distal portion of the closure device rotates a proximal access port defined in the proximal portion relative to a distal access port defined in the distal portion.

15. The method of claim 10, further including expanding at least one of the distal portion or the proximal portion into engagement with the tissue tract.

16. The method of claim 15, the tissue tract defining a lumen with an interior surface and wherein the proximal portion engages the interior surface of the lumen of the tissue tract.

* * * * *